(12) United States Patent
Hackam

(10) Patent No.: US 10,172,848 B2
(45) Date of Patent: Jan. 8, 2019

(54) GAP JUNCTION-ENHANCING AGENTS FOR TREATMENT OF NECROTIZING ENTEROCOLITIS AND INFLAMMATORY BOWEL DISEASE

(71) Applicant: University of Pittsburgh—of the Commonwealth System of Higher Education, Pittsburgh, PA (US)

(72) Inventor: David J. Hackam, Pittsburgh, PA (US)

(73) Assignee: UNIVERSITY OF PITTSBURGH—OF THE COMMONWEALTH SYSTEMS OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 13/921,865

(22) Filed: Jun. 19, 2013

(65) Prior Publication Data
US 2013/0345154 A1 Dec. 26, 2013

Related U.S. Application Data

(63) Continuation of application No. PCT/US2011/066861, filed on Dec. 22, 2011.

(60) Provisional application No. 61/426,152, filed on Dec. 22, 2010.

(51) Int. Cl.
| | | |
|---|---|---|
| *A61K 31/40* | (2006.01) | |
| *A61P 1/00* | (2006.01) | |
| *A61P 29/00* | (2006.01) | |
| *A61K 38/08* | (2006.01) | |
| *A61K 31/4709* | (2006.01) | |
| *A61K 38/07* | (2006.01) | |
| *A61K 38/10* | (2006.01) | |
| *A61K 38/16* | (2006.01) | |
| *A61K 31/47* | (2006.01) | |

(52) U.S. Cl.
CPC .......... *A61K 31/4709* (2013.01); *A61K 31/40* (2013.01); *A61K 31/47* (2013.01); *A61K 38/07* (2013.01); *A61K 38/08* (2013.01); *A61K 38/10* (2013.01); *A61K 38/16* (2013.01)

(58) Field of Classification Search
None
See application file for complete search history.

(56) References Cited

U.S. PATENT DOCUMENTS

| | | | |
|---|---|---|---|
| 4,357,322 A | 11/1982 | Rooks et al. | |
| 5,506,204 A | 4/1996 | Aston | |
| 5,756,718 A | 5/1998 | Christ et al. | |
| 5,962,636 A | 10/1999 | Bachmaier et al. | |
| 6,034,230 A | 3/2000 | Bachmaier et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,429,199 B1 | 8/2002 | Krieg et al. | |
| 6,544,518 B1 | 4/2003 | Friede et al. | |
| 6,558,670 B1 | 5/2003 | Friede et al. | |
| 6,613,751 B2 | 9/2003 | Raz et al. | |
| 6,652,392 B2 | 11/2003 | Higuchi et al. | |
| 7,038,029 B2 | 5/2006 | Lopez | |
| 7,049,302 B1 | 5/2006 | Kensil | |
| 7,129,222 B2 | 10/2006 | Van Nest et al. | |
| 7,183,111 B2 | 2/2007 | Van Nest et al. | |
| 7,250,397 B2* | 7/2007 | Larsen et al. | 514/16.4 |
| 7,348,316 B2 | 3/2008 | Rossignol et al. | |
| 7,744,884 B2 | 6/2010 | Elson | |
| 7,851,451 B2 | 12/2010 | Clandinin et al. | |
| 8,188,058 B2 | 5/2012 | Hackam et al. | |
| 8,518,903 B2 | 8/2013 | Hackam | |
| 8,518,905 B2 | 8/2013 | Hackam et al. | |
| 9,072,760 B2 | 7/2015 | Wipf et al. | |
| 2002/0064515 A1 | 5/2002 | Krieg et al. | |
| 2005/0250726 A1 | 11/2005 | Krieg et al. | |
| 2006/0211752 A1 | 9/2006 | Kohn et al. | |
| 2006/0241040 A1 | 10/2006 | Visintin et al. | |
| 2007/0004654 A1 | 1/2007 | Raz et al. | |
| 2008/0311112 A1 | 12/2008 | Hackam et al. | |
| 2009/0010902 A1 | 1/2009 | Masuda | |
| 2012/0077868 A1 | 3/2012 | Hackam | |
| 2013/0072547 A1 | 3/2013 | Hackam et al. | |
| 2013/0281395 A1 | 10/2013 | Wipf et al. | |
| 2013/0345154 A1 | 12/2013 | Hackam | |
| 2014/0086982 A1 | 3/2014 | Hackam | |
| 2014/0377238 A1 | 12/2014 | Budelli et al. | |
| 2015/0056217 A1 | 2/2015 | Hackam | |

FOREIGN PATENT DOCUMENTS

| | | |
|---|---|---|
| JP | 01-180894 | 7/1989 |
| WO | WO 98/18810 A1 | 5/1998 |
| WO | WO 98/37919 A1 | 9/1998 |
| WO | WO 98/52581 A1 | 11/1998 |
| WO | WO 99/33488 A2 | 7/1999 |
| WO | WO 2000/061555 | 10/2000 |
| WO | WO 2004/096156 | 11/2004 |

(Continued)

OTHER PUBLICATIONS

Ey et al., "TLR2 Mediates Gap Junctional Intercellular Communication through Connexin-43 in Intestinal Epithelial Barrier Injury," J. Biol. Chem. 284:22332-43 (2009).*

(Continued)

*Primary Examiner* — Julie Ha
*Assistant Examiner* — Kristina M Hellman
(74) *Attorney, Agent, or Firm* — Baker Botts L.L.P.

(57) ABSTRACT

The present invention relates to methods of reducing the risk of occurrence of, and/or treating, necrotizing enterocolitis ("NEC") or inflammatory bowel disease ("IBD") comprising administering, to a subject in need of such treatment, an effective amount of a gap junction enhancing agent ("GJEA"), for example a peptide ("GJP") or peptide analog ("GJPA"). It is based, at least in part, on the discovery that greater functionality of gap junctions between enterocytes increases their rate of migration and reduces the severity of intestinal inflammation.

15 Claims, 11 Drawing Sheets

Figure 1:
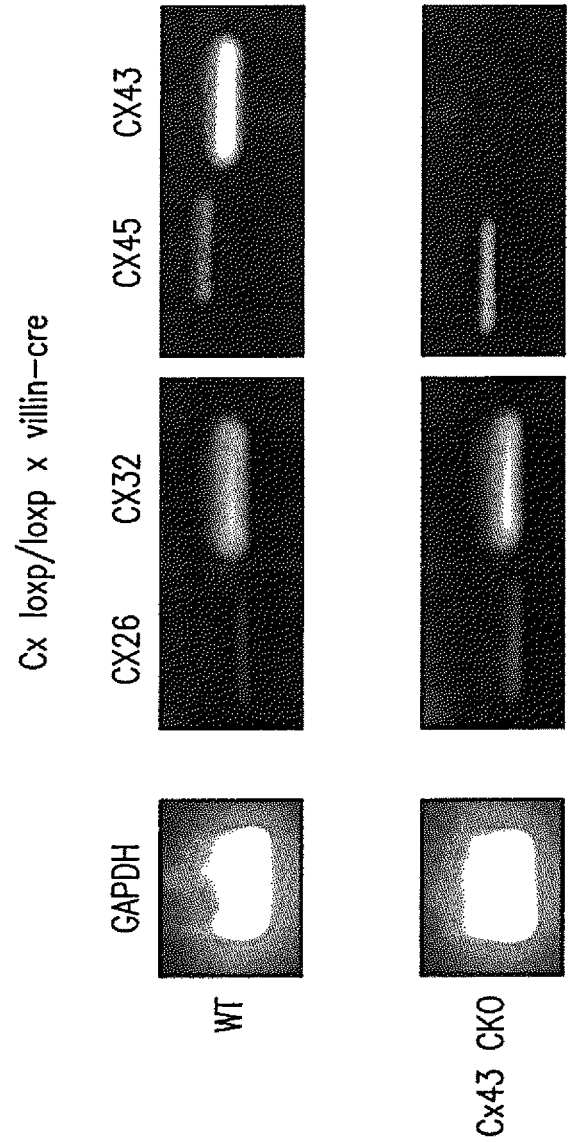

Specification includes a Sequence Listing.

(56) References Cited

FOREIGN PATENT DOCUMENTS

| WO | WO 2006/092049 | 9/2006 |
|---|---|---|
| WO | WO 2007/106886 | 9/2007 |
| WO | WO 2007/120368 | 10/2007 |
| WO | WO 2008/131074 A1 | 10/2008 |
| WO | WO 2014/052453 A1 | 4/2014 |

OTHER PUBLICATIONS

Ey et al., "Connexin-43 in Intestinal Epithelial Barrier Intercellular Communication through TLR2 Mediates Gap Junctional Injury," J. Biol. Chem. 284:22332-43 (Jun. 15, 2009).*
IEC-6 cells, Sigma Aldrich, accessed Aug. 2, 2016 at URL sigmaaldrich.com/catalog/product/sigma/88071401, 1 page.*
U.S. Appl. No. 12/104,816 (U.S. Pat. No. 8,188,058), filed Apr. 17, 2008 (May 29, 2012).
U.S. Appl. No. 13/068,553 (U.S. Pat. No. 8,518,903), filed May 13, 2011 (Aug. 27, 2013).
U.S. Appl. No. 13/461,672 (U.S. Pat. No. 8,518,905), filed May 1, 2012 (Aug. 27, 2013).
U.S. Appl. No. 14/036,960 (U.S. 2014/0086982), Sep. 25, 2013 (Mar. 27, 2014).
U.S. Appl. No. 14/010,232.
U.S. Appl. No. 13/848,809 (U.S. 2013/0281395), Mar. 22, 2013 (Oct. 24, 2013).
U.S. Appl. No. 12/104,816, May 14, 2013 Certificate of Correction.
U.S. Appl. No. 12/104,816, Apr. 23, 2012 Issue Fee payment.
U.S. Appl. No. 12/104,816, Jan. 23, 2012 Notice of Allowance.
U.S. Appl. No. 12/104,816, Nov. 10, 2011 Amendment and Request for Continued Examination (RCE).
U.S. Appl. No. 12/104,816, May 10, 2011 Final Office Action.
U.S. Appl. No. 12/104,816, Feb. 24, 2011 Response to Non-Final Office Action.
U.S. Appl. No. 12/104,816, Nov. 24, 2010 Non-Final Office Action.
U.S. Appl. No. 12/104,816, Sep. 15, 2010 Response to Restriction Requirement.
U.S. Appl. No. 12/104,816, Aug. 9, 2010 Restriction Requirement.
U.S. Appl. No. 13/068,553, Jul. 25, 2013 Issue Fee payment.
U.S. Appl. No. 13/068,553, Apr. 30, 2013 Notice of Allowance.
U.S. Appl. No. 13/068,553, Apr. 12, 2013 Response to Non-Final Office Action.
U.S. Appl. No. 13/068,553, Jan. 15, 2013 Non-Final Office Action.
U.S. Appl. No. 13/461,672, Jul. 25, 2013 Issue Fee payment.
U.S. Appl. No. 13/461,672, Apr. 29, 2013 Notice of Allowance.
U.S. Appl. No. 13/461,672, Apr. 12, 2013 Response to Non-Final Office Action.
U.S. Appl. No. 13/461,672, Jan. 14, 2013 Non-Final Office Action.
International Search Report for PCT/US2011/053293, dated Apr. 9, 2012.
Abreu et al., 2005, "TLR Signaling in the Gut in Health and Disease." J Immunol 174:4453-4460.
Achkar, "Ulcerative colitis: Responding to the challenges", Cleveland Clinic J. Med., 2007; 74(9):657-660.
Afrazi et al. "New insights into the pathogenesis and treatment of necrotizing enterocolitis: Toll-like receptors and beyond", Pediatr Res., 2011; 69:183-188.
Afrazi et al., "Intracellular heat shock protein-70 negatively regulates TLR4 signaling in the newborn intestinal epithelium", J. Immunol., 2012, 188:4543-4557.
Aki Tsukioka, "Eisai Successfully Completes Phase II Trial of Eritoran, Drug Candidate for Severe Sepsis." JCN Network, Aug. 30, 2005 p. 1. Downloaded on Nov. 20, 2009 from http://www.japancorp.net/printarticle.asp?Art_ID=10765.
Amer et al., "Platelet-activating factor concentration in the stool of human newborns: effects of enteral feeding and neonatal necrotizing enterocolitis", Biol Neonate, 2004; 85:159-166.
Anand et al., 2007, "The Role of the Intestinal Barrier in the Pathogenesis of Necrotizing Enterocolitis." Shock 27:124-133.

Anderson, 2001, "Infant, neonatal, and postnatal deaths, percent of total deaths, and mortality rates for the 10 leading causes of infant death by race and sex: United States: 1999." National Vital Statistics Reports. 49:73.
Blakely et al., "Postoperative outcomes of extremely low birth-weight infants with necrotizing enterocolitis or isolated intestinal perforation: a prospective cohort study by the NICHD Neonatal Research Network", Ann Surg. 2005; 241(6):984-989.
Borges et al., "Immune response by nasal delivery of hepatitis B surface and antigen and codelivery of a CpG ODN in alginate coated chitosan nanoparticles", European Journal of Pharmaceutics and Biopharmaceutics, 59:405-416 (2008).
Borzutzky et al., "NOD2-associated diseases: Bridging innate immunity and autoinflammation", Clin Immunol., 2010; 134:251-261.
Caplan et al., "The platelet activating factor receptor antagonist WEB 2170 prevents neonatal necrotizing enterocolitis in rats", J Pediatr Gastroenterol Nutr. 1997; 24:296-301.
Caplan et al., "The role of recombinant platelet activating factor acetylhydrolase in a neonatal rat model of necrotizing enterocolitis", Pediatr Res., 1997; 42:779-783.
Caplan et al., "Neonatal necrotizing entercolitis: possible role of probiotic supplementation", Journal of Pediatric Gastroenterology and Nutrition, 30(2):S18-S22 (2000).
Caradonna et al., "Phagocytosis, killing, lymphocyte-mediated anti-bacterial activity, serum autoantibodies, and plasma endotoxins in inflammatory bowel disease", Am J Gastroenterol. 2000; 95:1495-1502.
Career Opportunities—Eisai annuonces Phase II results, plans to initiate phase III clinical—Aug. 29, 2005. Downloaded on Apr. 18, 2007 from http://www.eisai.com/view_pressrelease.asp?ID=145&press=124.
Cario et al., 2000, "Lipopolysaccharide activates distinct signaling pathways in intestinal epithelial cell lines expressing Toll-like receptors." J Immunol. 164(2):966-72.
Carneiro et al., 2008, "Nod-like proteins in inflammation and disease." J Pathol. 214(2):136-48.
Cavallo et al., 2006 "The expression and function of enterocyte toll like receptor-4 are enhanced by lipopolysaccharide in vitro and during systemic endotoxemia." Association for academic surgery and society of university surgeons—Abstracts. Journal of Surgical Researchvol. 130, Issue 2, p. 232, No. 189.
Cetin et al., 2004, "Endotoxin inhibits intestinal epithelial restitution through activation of Rho-GTPase and increased focal adhesions." J Biol Chem. 279(23):24592-600. Epub Mar. 30, 2004.
Cetin et al., 2007, "Nitric oxide inhibits enterocyte migration through activation of RhoA-GTPase in a SHP-2-dependent manner." Am J Physiol Gastrointest Liver Physiol 292:G1347-1358.
Chan et al., "Role of LPS/CD14/TLR4-mediated inflammation in necrotizing enterocolitis: pathogenesis and therapeutic implications", World J Gastroenterol., 2009; 15:4745-4752.
Cho et al., 2007, "The genetics of inflammatory bowel disease." Gastroenterology 133:1327-1339.
Creagh et al., 2006, "TLRs, NLRs and RLRs: a trinity of pathogen sensors that co-operate in innate immunity." Trends Immunol. 27(8):352-7. Epub Jun. 27, 2006.
Dai et al., "Extracellular high mobility group box1 (HMGB1) inhibits enterocyte migration via activation of toll like receptor 4 and increased cell-matrix adhesiveness", J Biol Chem., 2010; 285:4995-5002.
Daubenberger, 2007, "TLR9 agonists as adjuvants for prophylactic and therapeutic vaccines." Curr. Opin. Molec. Ther. 9:45-52.
Ding et al., 1998, "Characterization and quantitation of NF-kappaB nuclear translocation induced by interleukin-1 and tumor necrosis factor-alpha. Development and use of a high capacity fluorescence cytometric system." J Biol Chem. 273(44):28897-905.
Diwan et al., "Enhancement of immune responses by co-delivery of a CpG oligodeoxynucleotide and tetanus toxoid in biodegradable nanospheres", J. Control Release, 85(1-3):247-262 (2002).
Duffy et al., "Concordance of bacterial cultures with endotoxin and interleukin-6 in necrotizing enterocolitis", Dig Dis Sci. 1997; 42:359-365.

(56) References Cited

OTHER PUBLICATIONS

Ewaschuk et al., 2007, "Surface expression of Toll-like receptor 9 is upregulated on intestinal epithelial cells in response to pathogenic bacterial DNA." Infect Immun. 75(5):2572-9. Epub Feb. 26, 2007.
Feng et al., "Heparin-binding epidermal growth factor-like growth factor promotes enterocyte migration and proliferation in neonatal rats with necrotizing enterocolitis", *J. Pediatr Surg.*, 2007; 42:214-220.
Feng et al., 2005, "Heparin-binding EGF-like growth factor (HB-EGF) and necrotizing enterocolitis." Semin Pediatr Surg. 14(3):167-74.
Franchi et al., 2008, "Intracellular NOD-like receptors in innate immunity, infection and disease." Cell Microbiol 10:1-8.
Fukata et al., "Cox-2 is regulated by Toll-like receptor-4 (TLR4) signaling: Role in proliferation and apoptosis in the intestine", *Gastroenterology*, 2006; 131:862-877.
Fukata et al., "Toll-like receptor-4 is required for intestinal response to epithelial injury and limiting bacterial translocation in a murine model of acute colitis", *Am J Physiol Gastrointest Liver Physiol.*, 2005; 288:G1055-G1065.
Fukata et al., "Innate immune signaling by Toll-like receptor-4 (TLR4) shapes the inflammatory microenvironment in colitis-associated tumors", *Inflamm Bowel Dis.* 2009; 15:997-1006.
Fukata et al., "TLR4 signaling in the intestine in health and disease", *Biochemical Society Transactions*, 35(6):1473-1478 (2007).
Gagliardi et al., "Necrotising enterocolitis in very low birth weight infants in Italy: incidence and non-nutritional risk factors", *J. Pediatr Gastroenterol Nutr.*, 2008; 47(2):206-210.
Goodenough, "Bulk isolation of mouse hepatocyte gap junctions. Characterization of the principal protein connexin", *J. Cell Biol.*, 1974; 61: 557-563.
Goodenough, "The structure of cell membranes involved in intercellular communication", *Am. J. Clin. Pathol.*, 1975; 63:636-645.
Grave et al., "New therapies and preventive approaches for necrotizing enterocolitis: report of a research planning workshop", *Pediatr Res.*, 2007; 62:510-514.
Gribar et al., "Reciprocal expression and signaling of TLR4 and TLR9 in the pathogenesis and treatment of necrotizing enterocolitis", *Journal of Immunologists*, 182(1):636-646 (2009).
Gribar et al., 2008, "The role of epithelial Toll-like receptor signaling in the pathogenesis of intestinal inflammation." J Leukoc Biol. 83(3):493-8. Epub Dec. 26, 2007.
Grimm et al., "NOD2 Mutations and Crohn's Disease: Are Paneth Cells and Their Antimicrobial Peptides the Link?" Gut; 53(11): 1558-1560, Nov. 2004, entire document especially p. 2.
Guthrie et al., 2003, "Necrotizing enterocolitis among neonates in the United States." J Perinatol 23:278-285.
Halpern et al., "Reduction of experimental necrotizing enterocolitis with anti-TNF-alpha", Am J Physiol Gastrointest Liver Physiol 290:757-764, 2006, First published Nov. 3, 2005, entire document especially abstract; p. 1.
Halpern et al., 2006, "Reduction of experimental necrotizing enterocolitis with anti-TNF-α." Am J. Physiol Gastrointest Liver Physiol 290, pp. G757-G764.
Henry et al., 2006, "Laparotomy Versus Peritoneal Drainage for Perforated Necrotizing Enterocolitis." Neoreviews 7:456-462.
Henry et al., 2005, "Surgical therapy for necrotizing enterocolitis: bringing evidence to the bedside." Semin Pediatr Surg. 14(3):181-90.
Hotta et al., "Lipopolysaccharide-induced colitis in rabbits", *Res Exp Med (Berl)* 1986; 186:61-69.
Hsueh et al., 2003, "Neonatal necrotizing enterocolitis: clinical considerations and pathogenetic concepts." Pediatr Dev Pathol 6:6-23.
Hugot et al., "Association of NOD2 leucine-rich repeat variants with susceptibility to Crohn's disease." Nature. 411(6837):599-603 (2001).
InvivoGen: Delivering Genes. "TLR9 Ligands." Downloaded on Apr. 16, 2007 from hrrp://www.invivogen.com/family.php?ID=104&ID_cat=2&ID_sscat=9.

Iwasaki et al., "Regulation of adaptive immunity by the innate immune system", *Science*, 2010; 327:291-295.
Izumi et al., "Platelet-activating factor receptor: gene expression and signal transduction", *Biochim Biophys Acta*, 1995; 1259:317-333.
Jesse et al., 2006, "Necotrizing enterocolitis: Relationship to Innate Immunity, Clinical Features, and Strategies for Prevention." NeoReviews 7:143-150.
Jilling et al., "The roles of bacteria and TLR4 in rat and murine models of necrotizing enterocolitis." J Immunol. 177(5):3273-82 (2006).
Kanneganti et al., 2007, "Intracellular NOD-like receptors in host defense and disease." Immunity 27:549-559.
Katakura et al., "Toll-like receptor 9-induced type I IFN protects mice from experimental colitis." J Clin Invest. 115(3):695-702. Erratum in: J Clin Invest. 2005 115(4):1100 (2005).
Kitagaki et al., "Oral administration of CpG-ODNs suppresses antigen-induced asthma in mice", *British Society for Immunology, Clinical and Experimental Immunology*, 143:249-259 (2005).
Knapp, et al., "Thionation: GlcNAc-Thiazoline Triacetate {(3aR,5R,6S,7R,7aR)-5-Acetoxymethyl-6, 7-Diacetoxy-2-Methyl-5,6,7,7a-Tetrahydro-3aH-Pyrano[3,2-d]Thiazole}", *Organic Syntheses*, 84:68-76 (2007).
Kobayashi et al., "Suppression of murine endotoxin response by E5531, a novel synthetic lipid A antagonist." Antimicrob Agents Chemother. 42(11):2824-9 (1998).
Kosloske, 1994, "Epidemiology of necrotizing enterocolitis." Acta Pediatr. Suppl. 396:2-7.
Krieg, 2006, "Therapeutic potential of Toll-like receptor 9 activation." Nat. Rev. Drug Disc. 5:471-484.
Kruis et al., "Circulating lipid A antibodies despite absence of systemic endotoxemia in patients with Crohn's disease", *Dig Dis Sci.*, 1984; 29:502-507.
Laird, "Connexin phosphorylation as a regulatory event linked to gap junction internalization and degradation", *Biochi. Biophys. Acta*, 2005; 1711: 172-182.
Lampe et al., "Phosphorylation of connexin-43 on serine 368 by protein kinase C regulates gap junction communication", *J. Cell Biol.*, (2000) 149:1503-1512.
Lee et al., 2006, "Homeostatic effects of TLR9 signaling in experimental colitis." Ann NY Acad Sci. 1072:351-5.
Leapart et al., "Interferon-γ inhibits enterocyte migration by reversibly displacing connexion43 from lipid rafts", *Am J Physiol Gastrointest Liver Physiol*, 2008; 295:G559-G569.
Leaphart et al., 2007. "A Critical Role for TLR4 in the Pathogenesis of Necrotizing Enterocolitis by Modulating Intestinal Injury and Repair." J Immunology 179:4808-4820.
Leaphart et al., 2007, "Interferon-gamma inhibits intestinal restitution by preventing gap junction communication between enterocytes." Gastroenterology. 132(7):2395-411. Epub Mar. 21, 2007.
Lemaitre et al., "The dorsoventral regulatory gene cassette spatzle/Toll/cactus controls the potent antifungal response in *Drosophila* adults", *Cell*, 1996; 86:973-983.
Lin et al., "Oral probiotics reduce the incidence and severity of necrotizing enterocolitis in very low birth weight infants", *Pediatrics*, 2005; 115:1-4.
Lin et al., 2006, "Necrotising enterocolitis." Lancet 368:1271-1283.
Liu et al., "Changes in intestinal toll-like receptors and cytokines precede histological injury in a rat model of necrotizing enterocolitis", *Am J Physiol Gastrointest Liver Physiol.*, 2009; 297:G442-G450.
Lotz et al., "Postnatal acquisition of endotoxin tolerance in intestinal epithelial cells", *J Exp Med.*, 2006; 203:973-984.
Lu et al., "Polyunsaturated fatty acid supplementation alters proinflammatory gene expression and reduces the incidence of necrotizing enterocolitis in a neonatal rat model", *Pediatr Res.*, 2007; 61:427-432.
Luig et al., "Epidemiology of necrotizing enterocolitis—PartI: Changing regional trends in extremely preterm infants over 14 years", *J. Paediatr Child Health*, 2005; 41(4):169-73.
Macagno et al., 2006, "A cyanobacterial LPS antagonist prevents endotoxin shock and blocks sustained TLR4 stimulation required for cytokine expression." J. Exp. Med. 203(6):1481-1492.

(56) References Cited

OTHER PUBLICATIONS

Maeda et al., 2005, "Nod2 mutation in Crohn's disease potentiates NF-kappaB activity and IL-1beta processing." Science 307:734-738. Erratum in Science. Apr. 29, 2005;308(5722):633.
Medzhitov et al., "A human homologue of the *Drosophila* Toll protein signals activation of adaptive immunity", *Nature*, 1997; 388:394-397.
Merck Manual website, Nov. 2007 by William J. Cochran, MD. Downloaded on Nov. 7, 2011 from <http://www.merckmanuals.com/professional/pediatrics/gastrointestinal_disorders_in_neonates_and_infants/necrotizing_enterocolitis.html>.
Michaelsson et al., "Regulation of T cell responses in the developing human fetus", *J. Immunol.*, 2006; 176(10):5741-5748.
Milla et al., "Small intestinal motility patterns in the perinatal period", *J Pediatr. Gastroenterol Nutr.*, 1983; 2:S141-S144.
Mizrahi et al., "Necrotizing enterocolitis in premature infants", *J Pediatr.*, 1965; 66:697-705.
Moss et al., 2006, "Laparotomy versus peritoneal drainage for necrotizing enterocolitis and perforation." N. Engl. J. Med. 354:2225-2234.
Muguruma et al., "The central role of PAF in necrotizing enterocolitis development", *Adv Exp Med Biol.* 1997; 407:379-382.
Mullarkey et al., 2003, "Inhibition of endotoxin response by e5564, a novel Toll-like receptor 4-directed endotoxin antagonist." J Pharmacol Exp Ther. 304(3):1093-102.
Neal et al., "A critical role for TLR4 induction of autophagy in the regulation of enterocyte migration and the pathogenesis of necrotizing enterocolitis", *J. Immunol.*, 2013; 190(7):3541-3551.
Neal et al., "Enterocyte TLR4 mediates phagocytosis and translocation of bacteria across the intestinal barrier." J Immunol. 176(5):3070-9 (2006).
Neu et al., 2005, "Intestinal innate immunity: how does it relate to the pathogenesis of necrotizing enterocolitis." Semin. Pediatr. Surg. 14: 137-144.
Neu, 1996, "Necrotizing enterocolitis: the search for a unifying pathogenic theory leading to prevention." Pediatr Clin North Am. 43(2):409-32.
Ng, 2001, "Necrotizing enterocolitis in the full-term neonate." J Paediatr Child Health. 37(1):1-4.
Noerr, "Current controversies in the understanding of necrotizing enterocolitis", *Adv Neonatal Care*, 2003; 3:107-120.
Obermeier et al., "Contrasting activity of cytosin-guanosin dinucleotide oligonucleotides in mice with experimental colitis", *Clin Exp Immunol.*, 134(2):217-224 (2003).
Obermeier et al. 2002, "CpG motifs of bacterial DNA exacerbate colitis of dextran sulfate sodium-treated mice." Eur J Immunol. Jul. 2002;32(7):2084-92.
Ogura et al., "A frameshift mutation in NOD2 associated with susceptibility to Crohn's disease." Nature. 411(6837):603-6 (2001).
Otte et al., 2004, "Mechanisms of cross hyporesponsiveness to Toll-like receptor bacterial ligands in intestinal epithelial cells." Gastroenterology. 126(4):1054-70.
Panigrahi, "Necrotizing enterocolitis", *Paediatr. Drugs*, 2006; 8(3):151-165.
Pierro, 2005, "The surgical management of necrotising enterocolitis." Early Hum Dev. 81(1):79-85.
Poltorak et al., 1998, "Defective LPS Signaling in C3H/HeJ and C57BL/10ScCr Mice: Mutations in Tlr4 Gene." Science 282: 2085-2088.
Prohinar et al., "Specific high affinity interactions of monomeric endotoxin protein complexes with Toll-like receptor 4 ectodomain." J Biol Chem. 282(2):1010-7. (2007).
Putta et al., 2006, "Novel oligodeoxynucleotide agonists of TLR9 containing N3-Me-dC or N1-Me-dG modifications." Nucleic Acids Res. 34(11):3231-8.
Qureshi et al., "Increased expression and function of integrins in enterocytes by endotoxin impairs epithelial restitution", *Gastroenterology*, 2005; 128:1012-1022.

Rachmelewitz et al., 2004, "Toll-like receptor 9 signaling mediates the anti-inflammatory effects of probiotics in murine experimental colitis." Gastroenterology. 126(2):520-8.
Rakoff-Nahoum et al., "Recognition of commensal microflora by toll-like receptors is required for intestinal homeostasis", *Cell*, 2004; 118:229-241.
Richardson, et al., "Nucleotide-binding Oligomerization Domain-2 Inhibits Toll Like Receptor-4 Signaling in the Intestinal Epithelium", *Gastroenterology*, 139(3):904-917 (2010).
Roach et al., "The evolution of vertebrate Toll-like receptors", PNAS, 2005; 102:9577-9582.
Rossignol et al., 2004, "Safety, pharmacokinetics, pharmacodynamics, and plasma lipoprotein distribution of eritoran (E5564) during continuous intravenous infusion into healthy volunteers." Antimicrob Agents Chemother. 48(9):3233-40.
Sodhi, et al., "DNA Attenuates Enterocyte Toll-like Receptor 4-Mediated Intestinal Mucosal Injury After Remote Trauma", *Am J Physiol Gastrointest Liver Physiol.*, 300:G862-G873 (2011).
Sodhi, et al., "Toll-like-receptor-4 Inhibits Enterocyte Proliferation via Impaired β-Catenin Signaling in Necrotizing Enterocolitis", *Gastroenterology*, 138(1):185-196 (2010).
Shan et al., "Regulation of toll-like receptor 4-induced proasthmatic changes in airway smooth muscle function by opposing actions of ERK1/2 and p38 MAPK signaling", *Am J. Physiol. Lung Cell Mol. Physiol.*, 291(3):L324-L333 (2006).
Sharma et al., 2007, "Neonatal gut barrier and multiple organ failure: role of endotoxin and proinflammatory cytokines in sepsis and necrotizing enterocolitis." J Pediatr Surg 42:454-461.
Shin et al., 2000, "Diminished epidermal growth factor levels in infants with necrotizing enterocolitis." J Pediatr Surg. 35(2):173-6; discussion 177.
Shindou et al., "Roles of cytosolic phospholipase A2 and platelet-activating factor receptor in the Ca-induced biosynthesis of PAF", *Biochem Biophys Res Commun.* 2000; 271:812-817.
Shuto et al., "Activation of NF-kappa B by nontypeable hemophilus influenzae is mediated by toll-like receptor 2-TAK1-dependent NIK-IKK alpha/beta-I kappa B alpha and MKK3/6-p38 MAP kinase signaling pathways in epithelial cells", *PNAS*, 98(15):8774-8779 (2001).
Strober et al., 2006, "Signalling pathways and molecular interactions of NOD1 and NOD2." Nat Rev Immunol. 6:9-20.
Supplemental European Search Report for EP Application No. 08746070.5, dated May 25, 2011.
Svetlov et al., "Regulation of platelet-activating factor (PAF) biosynthesis via coenzyme A-independent transacylase in the macrophage cell line IC-21 stimulated with lipopolysaccharide", *Biochim Biophys Acta*, 1997; 1346:120-130.
Takeda et al., "Toll-like receptors in innate immunity." Int Immunol. 17(1):1-140, 2005.
Takeda et al., 2001, "Roles of Toll-like receptors in innate immune responses." Genes Cells 6:733-742.
Tatum et al., "The role of toll-like receptor 9 in an animal model of necrotizing entercolitis", *Journal of Investigative Medicine*, 58(2):436 (2010).
Thompson et al., "Necrotizing enterocolitis in newborns", *Drugs*, 2008; 68(9):1227-1238.
Wolfs et al., "Localization of the lipopolysaccharide recognition complex in the human healthy and inflamed premature and adult gut", *Inflamm Bowel Dis.*, 2010; 16:68-75.
Uauy et al., 1991, "Necrotizing enterocolitis in very low birth weight infants: biodemographic and clinical correlates." National Institute of Child Health and Human Development Neonatal Research Network. J Pediatr 119:630-638.
University of Pittsburgh Department of Critical Care Medicine: Research-The Crisma Laboratory, pp. 1-11. Downloaded on Apr. 19, 2007 from http:/www.ccm.upmc.edu/research/res_crisma.htlm.
Van Heel et al., "Synergy between TLR9 and NOD2 innate immune responses is lost in genetic Chrohn's disease" *GUT, British Medical Association*, 54(11):1553-1557 (2005).
Verma et al., "Novel pharmacophores of connexin-43 based on the "RXP" series of Cx43-binding peptides", *Circ. Res.*, 2009; 105(2):176-184.

(56) References Cited

OTHER PUBLICATIONS

Verthelyi et al., "Human peripheral blood cells differentially recognize and respond to two distinct CPG motifs." J Immunol. 166(4):2372-7 (2001).
Vink et al., 2002, "In vivo evidence for a role of toll-like receptor 4 in the development of intimal lesions." Circulation. 106(15):1985-90.
Wang et al., "NF-κB-mediated expression of MAPK phosphatase-1 is an early step in desensitization to TLR ligands in enterocytes", *Mucosal Immunol.*, 2010; 3:523-534.
Wang et al., "Ubiquitin-editing enzyme A20 promotes tolerance to lipopolysaccharide in enterocytes", *J Immunol.*, 2009; 183:1384-1392.
Warner et al., 2005, "Role of epidermal growth factor in the pathogenesis of neonatal necrotizing enterocolitis." Semin Pediatr Surg. 14(3):175-80.
Watanabe et al., "Muramyl dipeptide activation of nucleotide-binding oligomerization domain 2 protects mice from experimental colitis." J Clin Invest 118:545-559 (2008).
Wirtz et al., "Illuminating the role of type I IFNs in colitis." J Clin Invest. 115(3):586-8 (2005).
Worthen et al., "The priming of neutrophils by lipopolysaccharide for production of intracellular platelet-activating factor: potential role in mediation of enhanced superoxide secretion", *J Immunol.*, 1988; 140:3553-3559.
Wynn et al., "The host response to sepsis and developmental impact", *Pediatrics*, 2010; 125:1031-1041.
Yang et al., "NOD2 transgenic mice exhibit enhanced MDP-mediated down-regulation of TLR2 responses and resistance to colitis induction." Gastroenterology 133:1510-1521 (2007).
Yang et al., 2005, "Role of Toll-like receptor 4/NF-kappaB pathway in monocyte-endothelial adhesion induced by low shear stress and ox-LDL." Biorheology. 42(3):225-36.
Yang et al., 2007, "NOD2 pathway activation by MDP or *Mycobacterium tuberculosis* infection involves the stable polyubiquitination of Rip2." J Biol Chem 282:36223-36229.
Zhai et al., "Cutting edge: TLR4 activation mediates liver ischemia/reperfusion inflammatory response via IFN regulatory factor 3-dependent MyD88-independent pathway", *J. Immunol.*, 173(12):7115-7119 (2004).
Zheng et al., "Regulation of colonic epithelial repair in mice by Toll-like receptors and hyaluronic acid", *Gastroenterology*, 2009; 137:2041-2051.
Zhou et al., "Oral administration of plant-based rotavirus VP6 induces antigen-specific IgAs, IgGs and passive protection in mice" *Vaccine*, 28:6021-6027 (2010).
U.S. Appl. No. 14/010,232 (U.S. 2015/0056217), filed Aug. 26, 2013 (Feb. 26, 2015).
U.S. Appl. No. 13/848,809, May 12, 2015 Issue Fee Payment.
U.S. Appl. No. 13/848,809, Feb. 17, 2015 Notice of Allowance.
U.S. Appl. No. 13/848,809, Feb. 3, 2015 Request for Continued Examination (RCE).
U.S. Appl. No. 13/848,809, Nov. 10, 2014 Notice of Allowance.
U.S. Appl. No. 14/010,232, Sep. 21, 2015 Response to Non-Final Office Action.
U.S. Appl. No. 14/010,232, Jun. 19, 2015 Non-Final Office Action.
U.S. Appl. No. 14/010,232, May 27, 2015 Response to Restriction Requirement.
U.S. Appl. No. 14/010,232, Feb. 27, 2015 Restriction Requirement Filed.
U.S. Appl. No. 14/036960, Apr. 20, 2016 Non-Final Office Action.
U.S. Appl. No. 14/036,960, Jan. 4, 2016 Response to Non-Final Office Action.
U.S. Appl. No. 14/036,960, Oct. 1, 2015 Non-Final Office Action.
U.S. Appl. No. 14/036,960, Jul. 9, 2015 Response to Non-Final Office Action.
U.S. Appl. No. 14/036,960, Jan. 12, 2015 Non-Final Office Action.
U.S. Appl. No. 14/036,960, Dec. 22, 2014 Response to Restriction Requirement.
U.S. Appl. No. 14/036,960, Sep. 23, 2014 Restriction Requirement Filed.
Abreu, "Toll-like receptor signalling in the intestinal epithelium: how bacterial recognition shapes intestinal function," Nature Reviews/Immunology, Feb. 2010, 10:131-143.
Arciero et al., "Modeling the interactions of bacteria and Toll-like receptor-mediated inflammation in necrotizing enterocolitis," Journal of Theoretical Biology, 2013, 321:83-99.
Hackam et al., "Mechanisms of gut barrier failure in the pathogenesis of necrotizing enterocolitis: Toll-like receptors throw the switch," Semin Pediatr Surg 22(2): 76-82, May 2013.
Henckaerts et al., "NOD/CARD15 Disease Associations Other Than Crohn's Disease," Inflamm Bowel Dis 13(2): 235-241, 2007.
Lavelle et al., "The role of TLRs, NLRs, and RLRs in mucosal innate immunity and homeostasis," Mucosal Immunol 3(1): 17-28, Jan. 2010.
Parant et al., "Stimulation of Non-Specific Resistance to Infections by Synthetic Immunoregulatory Agents," Infection 12(3): 230-234, 1984.
Sartor, "Targeting enteric bacteria in treatment of inflammatory bowel diseases: why, how, and when," Current Opinion in Gastroenterology 2003, 19:358-365.
Zouali et al., "CARD15/NOD2 is Not a Predisposing Factor for Necrotizing Enterocolitis," Digestive Diseases and Sciences 50(9): 1684-1687, 2005.
U.S. Appl. No. 14/036,960, Dec. 21, 2016 Issue Fee Payment.
U.S. Appl. No. 14/036,960, Oct. 26, 2016 Notice of Allowance.
U.S. Appl. No. 14/036,960, Jul. 20, 2016 Response to Non-Final Office Action.
U.S. Appl. No. 14/010,232, Nov. 23, 2016 Issue Fee Payment.
U.S. Appl. No. 14/010,232, Sep. 28, 2016 Notice of Allowance.
U.S. Appl. No. 14/010,232, Aug. 10, 2016 Amendment and Request for Continued Examination (RCE).
U.S. Appl. No. 14/010,232, May 10, 2016 Final Office Action.
Good et al., "Evidence based feeding strategies before and after the development of necrotizing enterocolitis," Expert Rev Clin Immunol., Jul. 2014; 10(7):875-884.
U.S. Appl. No. 14/717,349 (U.S. Pat. No. 9,532,999), filed May 20, 2015 (Jan. 3, 2017).
U.S. Appl. No. 15/383,625 (U.S. 2017/0095493), filed Dec. 19, 2016 (Apr. 6, 2017).
U.S. Appl. No. 14/717,349, Nov. 22, 2016 Issue Fee Payment.
U.S. Appl. No. 14/717,349, Aug. 29, 2016 Notice of Allowance.
U.S. Appl. No. 14/717,349, Aug. 15, 2016 Response after Final Office Action.
U.S. Appl. No. 14/717,349, May 26, 2016 Final Office Action.
U.S. Appl. No. 14/717,349, Mar. 10, 2016 Response to Non-Final Office Action.
U.S. Appl. No. 14/717,349, Dec. 10, 2015 Non-Final Office Action.

\* cited by examiner

Connexin 43 CKO are less able to absorp fat from their diet

| | Fecal fat | Protein | Glucose |
|---|---|---|---|
| WT | 1.02% | 16.45% | 1.4523µg/mg |
| Cx43 CKO | 9.27% | 14.65% | 1.374µg/mg |

FIG. 4

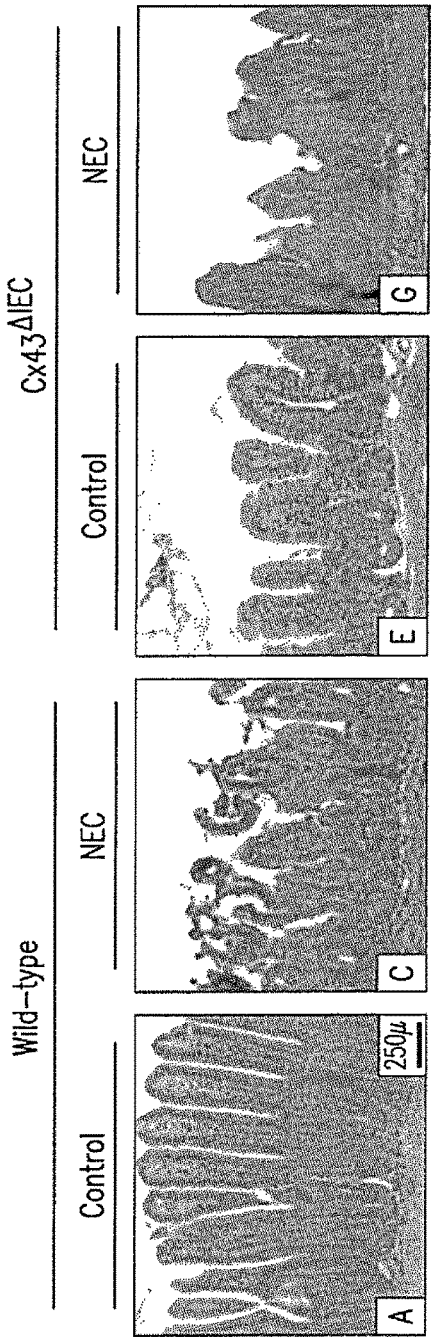

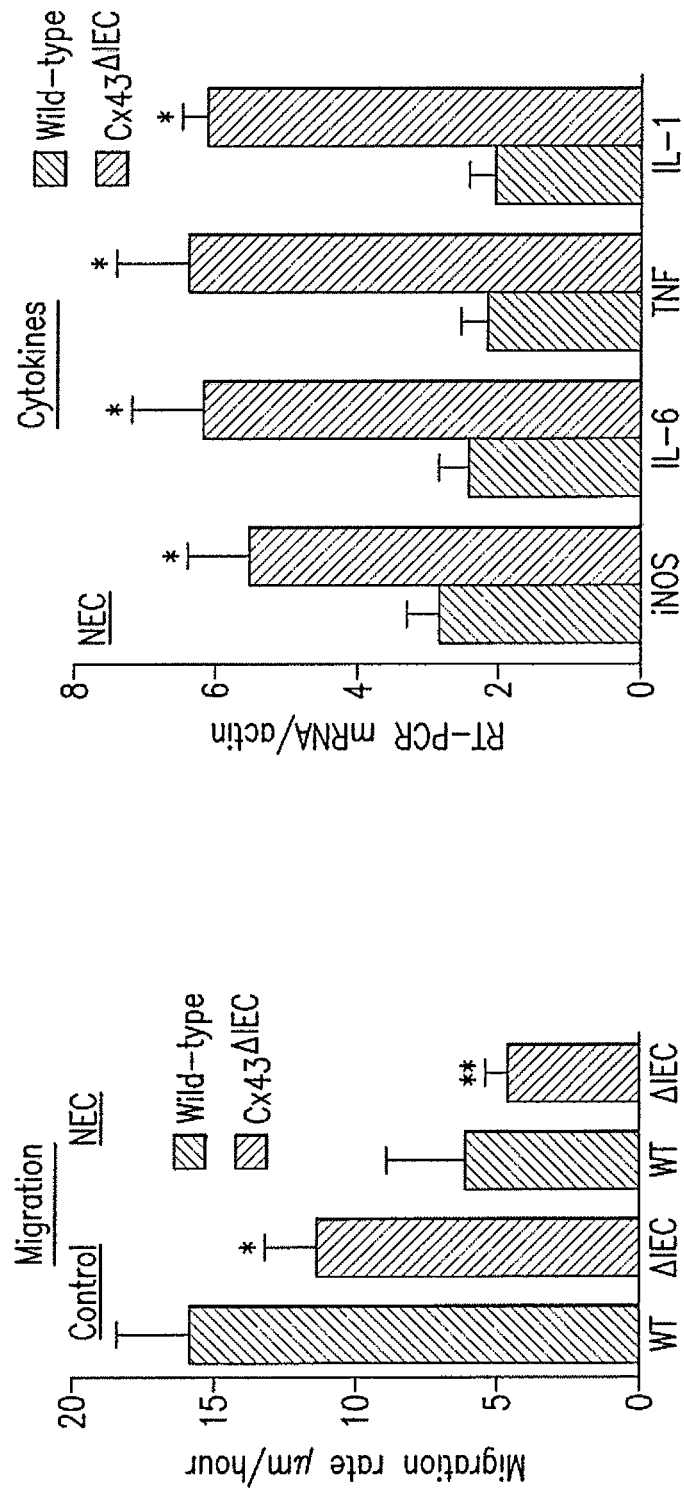

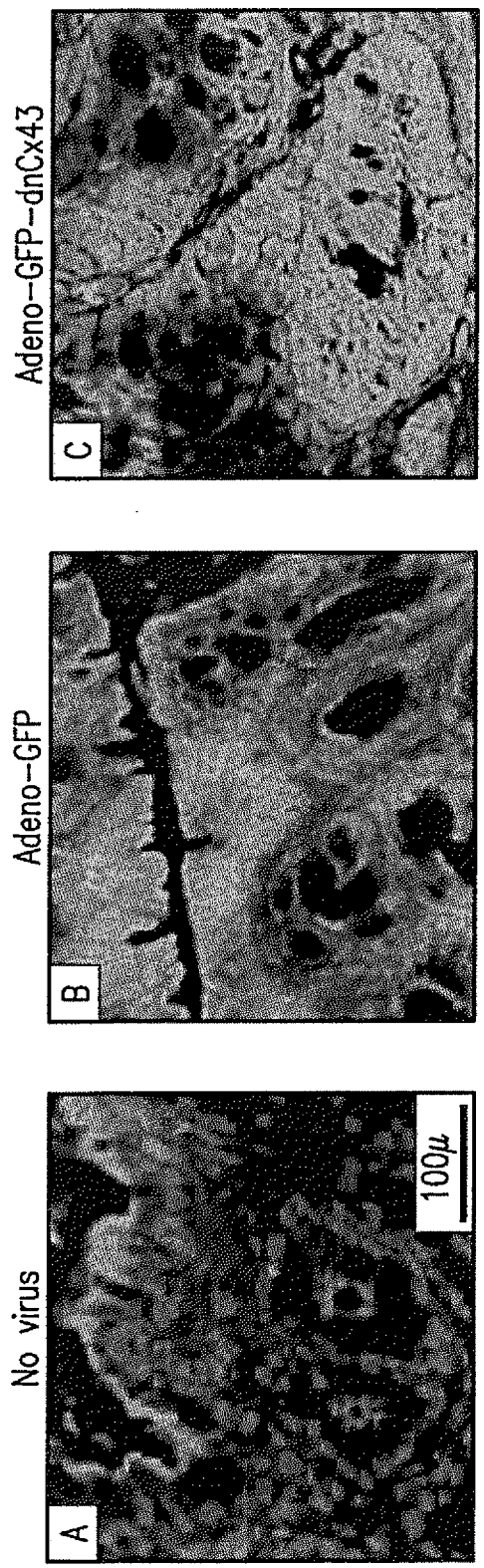

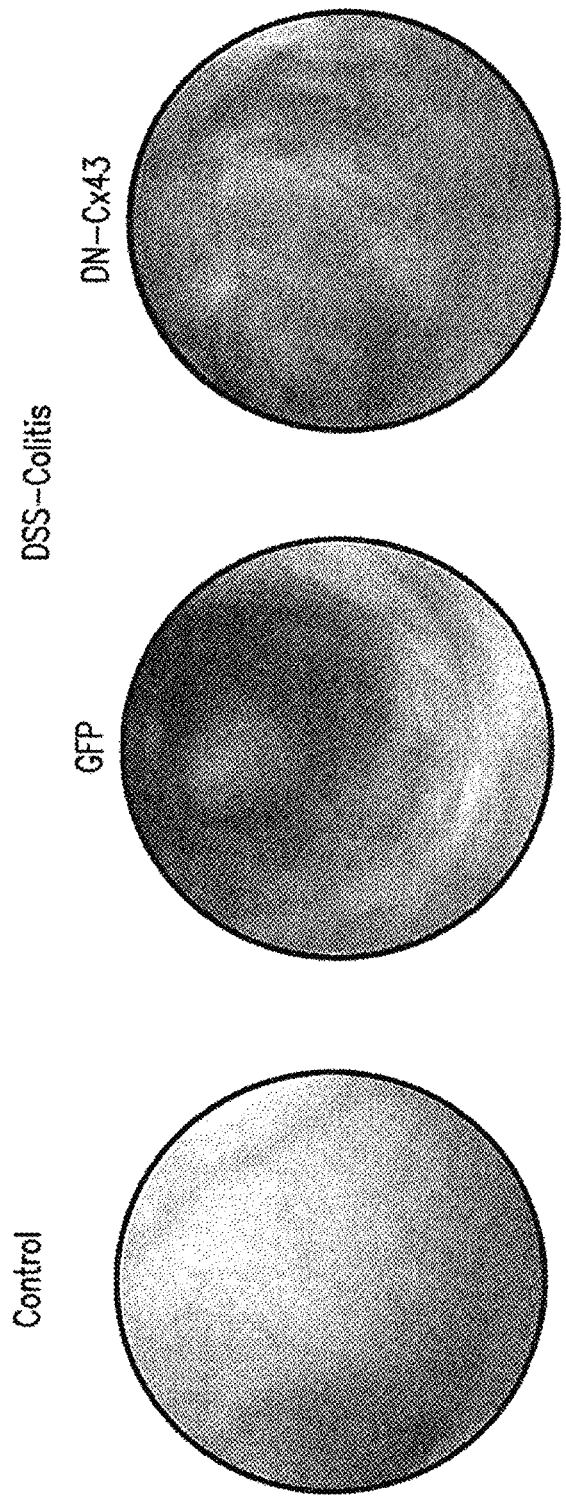

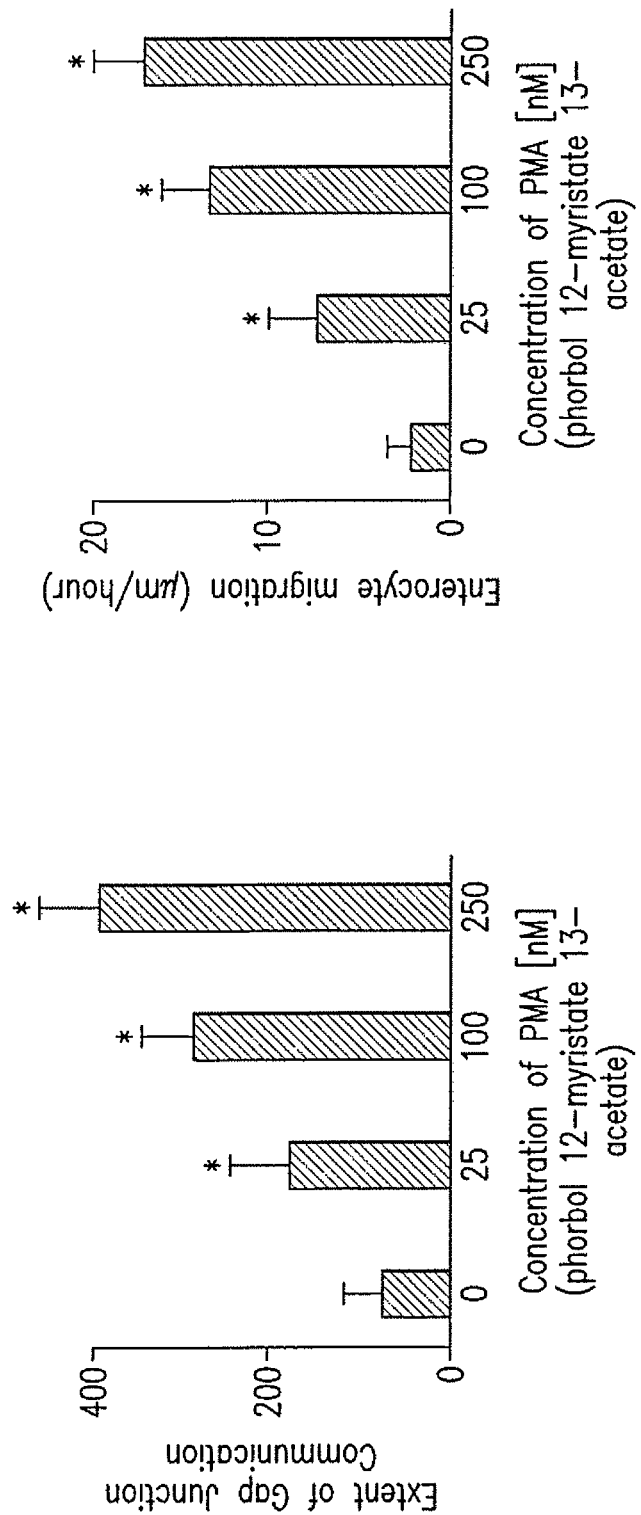

SEQUENCE LISTING

<160> NUMBER OF SEQ ID NOS: 31

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Val Pro Gly Arg Asp Pro Gly Tyr Ile Lys Gly Gly Gly Ser Ala
1               5                   10                  15

His Ala Arg Val Pro Phe Tyr Ser His Ser Leu Asn Arg Asn Arg Lys
            20                  25                  30

Pro Ser Leu Tyr Gln
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Gln Pro Arg Ser Pro Leu Met Phe Ser Gly Gly Gly Ser Ala
1               5                   10                  15

His Ala Arg Val Pro Phe Tyr Ser His Ser Ala Lys Glu Ala Arg Trp
            20                  25                  30

Pro Arg Ala His Arg
        35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Ile Ala Ala Arg Glu Pro Asn Ser His Asp Gly Gly Gly Ser Ala
1               5                   10                  15

His Ala Arg Val Pro Phe Tyr Ser His Ser Arg Asp Leu Trp Arg Lys
            20                  25                  30

Pro Ala Lys Ser Leu
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Trp Glu Glu Pro Arg Arg Pro Phe Thr Met Ser Gly Gly Gly Ser Ala
1               5                   10                  15

Glu Thr His Ala Arg Val Pro Phe Tyr Ser His Ser Pro Met Arg His
            20                  25                  30

```
Arg Leu Pro Gly Val His Leu
        35
```

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Ser Asp Asp Leu Arg Ser Pro Gln Leu His Asn Gly Gly Ser Ala
1               5                   10                  15

Val Pro Phe Tyr Ser His Ser His Met Val Arg Arg Lys Pro Arg Asn
            20                  25                  30

Pro Arg
```

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly His Leu His Leu Arg Val Pro Thr Leu Lys Met
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Glu Phe Ile Arg Ser Pro His Ser Val Asp Trp Leu
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ser Gln Ser Arg Asn Pro Pro Met Pro Pro Pro Arg
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Arg Arg Pro Pro Tyr Arg Val Pro Pro Lys Leu Phe
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Leu Tyr Glu Arg His Pro Ala Ser Thr Tyr Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Thr Val Ser Arg Arg Pro Leu Pro Ser Ser Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg His Thr His Gly Asn Leu Leu Arg Phe Pro Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Asn Asn Leu Asn Gln Thr Tyr Pro Glu Arg Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ser Leu Leu Pro Val Arg Pro Val Ala Leu Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Arg Lys Pro Thr Gln Ser Leu Pro Thr Arg Leu Val
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Thr Arg Arg Pro His Lys Met Arg Ser Asp Pro Leu
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Thr Leu Thr Trp His Thr Lys Thr Pro Val Arg Pro
1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Ser Arg Gln Phe Leu His Ser Leu Asp Arg Leu Pro
1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
His Leu His His His Leu Asp His Arg Pro His Arg
1               5                   10
```

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gln Thr Pro Tyr Gln Ala Arg Leu Pro Ala Val Ala
1               5                   10
```

<210> SEQ ID NO 21
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 21

Trp His Pro His Arg His His His Leu Gln Trp Asp
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Lys Pro Arg Arg Lys Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Asn Pro Arg Asn Pro
1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Lys Pro
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Asn Pro
1

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Asp Asp Leu Arg Ser Pro Gln Leu His Asn His Met Val Arg Arg
1               5                   10                  15
```

```
Lys Pro Arg Asn Pro Arg
            20

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 27

Arg Xaa Pro Glu
1

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Asn Tyr Arg Arg Asn Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<223> OTHER INFORMATION: C-term NH2

<400> SEQUENCE: 29

Gly Ala Gly Pro Pro Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 30

Gly Pro Pro Gly Ala Gly
1               5

<210> SEQ ID NO 31
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term CF(3)C(OH)
<220> FEATURE:
<221> NAME/KEY: misc_feature
<222> LOCATION: (1)..(6)
<223> OTHER INFORMATION: Cyclic
<220> FEATURE:
<221> NAME/KEY: MOD_RES
<222> LOCATION: (4)..(4)
<223> OTHER INFORMATION: Hydroxyproline

<400> SEQUENCE: 31

Gly Ala Gly Pro Pro Tyr
1               5
```

GAP JUNCTION-ENHANCING AGENTS FOR TREATMENT OF NECROTIZING ENTEROCOLITIS AND INFLAMMATORY BOWEL DISEASE

PRIORITY

This application is a continuation of International Application No. PCT/US2011/066861, filed Dec. 22, 2011, and claims priority to U.S. Provisional Application No. 61/426,162, filed Dec. 22, 2010, the contents of which are expressly incorporated by reference herein.

SEQUENCE LISTING

The specification further incorporates by reference the Sequence Listing submitted herewith via EFS on Sep. 5, 2013. Pursuant to 37 C.F.R. § 1.52(e)(5), the Sequence Listing text file, identified as 0723960524_SL.txt, is 9,249 bytes and was created on Jul. 29, 2013. The Sequence Listing, electronically filed herewith, does not extend beyond the scope of the specification and thus does not contain new matter.

1. INTRODUCTION

This application relates to agents, particularly peptides and peptide analogs, that enhance the functionality of gap junctions between intestinal enterocytes, and which may be used to treat disorders associated with impaired interenterocyte gap junctions such as necrotizing enterocolitis and inflammatory bowel diseases. These gap junction enhancing peptides may also be used to reduce the risk of occurrence of these disorders.

2. BACKGROUND OF THE INVENTION

Necrotizing enterocolitis (NEC) is a leading cause of death and disability in premature infants. Patients that develop NEC do so suddenly and without warning, and upon surgical exploration of the abdomen, frequently demonstrate large regions of the intestine that are either dead or dying. In over half the cases, patients that develop NEC do not survive their disease, and in survivors, an additional third will develop long term complications related to the initial development of the disease. Currently, there is no specific therapy for NEC, and treatment involves the administration of broad spectrum antibiotics and surgical removal of the dead or dying intestine. Clearly, novel therapeutic approaches to this devastating disease are urgently needed.

In seeking to understand the pathogenesis of NEC, as well as to define novel therapeutic approaches for this disease, it was found that NEC is characterized by impaired enterocyte migration along the crypt-villus axis. The impaired enterocyte migration results in persistent mucosal defects, bacterial translocation, and the development of systemic sepsis which leads to death in many cases. In seeking to define the mechanisms that regulate enterocyte migration in both mice and humans, it was found that enterocytes migrate together as sheets, and that enterocyte migration is dependent upon intact inter-enterocyte communication via Cx43-mediated gap junctions (1, 2). Furthermore, the release of the pro-inflammatory cytokine interferon gamma (IFNγ) plays a critical role in the impairment of mucosal healing in part by inhibiting gap junctions between enterocytes (1, 2).

In other studies, it has been shown that human inflammatory bowel disease ("IBD") is associated with impaired gap junctions within the intestinal mucosa (1, 2). Enterocyte migration is impaired in IBD just as it is in NEC.

Gap junctions are intercellular channels that exist between adjacent cells which allow the transfer of small molecules between adjoining cells. Each gap junction channel is comprised of a pair of hexameric arrays of individual subunits called connexins, of which the most widely expressed isoform is connexin-43 (Cx43; 2, 3, 4). The function of gap junctions is regulated in part through phosphorylation of the individual connexin molecules, which serves to regulate the localization of the channels at the plasma membrane as well as to regulate the channel through gating (5, 6).

3. SUMMARY OF THE INVENTION

The present invention relates to methods of reducing the risk of occurrence of, and/or treating, necrotizing enterocolitis ("NEC") or inflammatory bowel disease ("IBD") comprising administering, to a subject in need of such treatment, an effective amount of a gap junction enhancing agent ("GJEA"), for example a peptide ("GJP") or peptide analog ("GRA"). It is based, at least in part, on the discovery that greater functionality of gap junctions between enterocytes increases their rate of migration and reduces the severity of intestinal inflammation.

4. BRIEF DESCRIPTION OF THE DRAWINGS

FIG. 1. Cx43 knockout "cko" mice were generated. RT-PCR demonstrated the absence of Cx43.

Figures 2A, 2B:
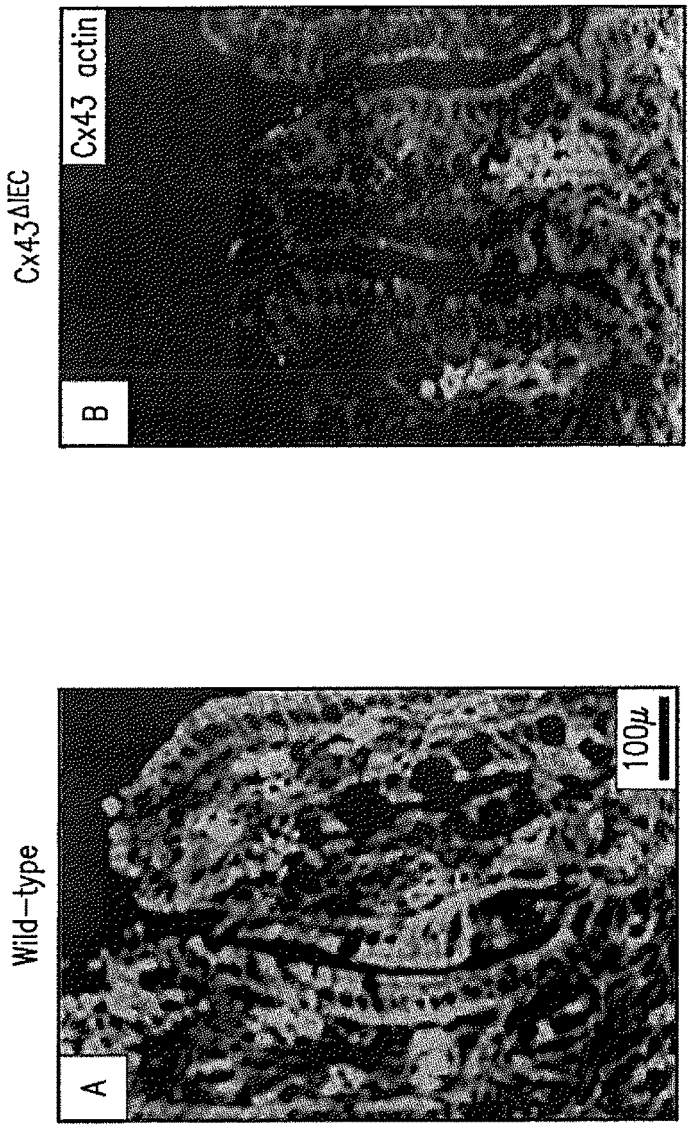

FIG. 2A-B. Immunohistochemistry studies using fluorescently labeled antibodies directed toward Cx43 and actin demonstrate (A) the presence of both proteins in wild-type intestinal villi and (B) the absence of Cx43 in the villi of knock-out animals having the selective deletion of Cx43.

Figure 3A:
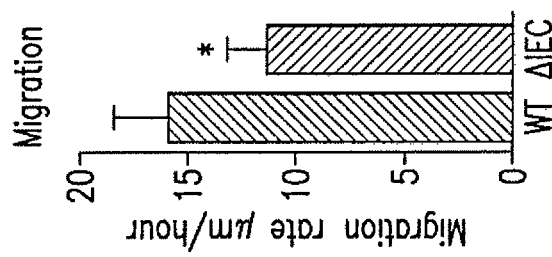
Figure 3B:
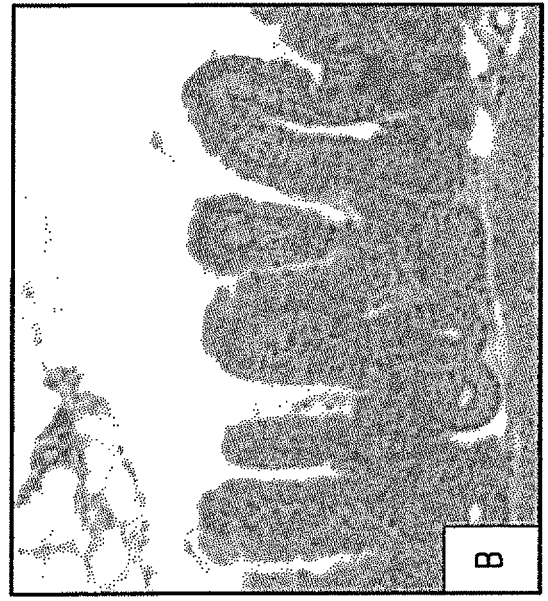
Figure 3C:
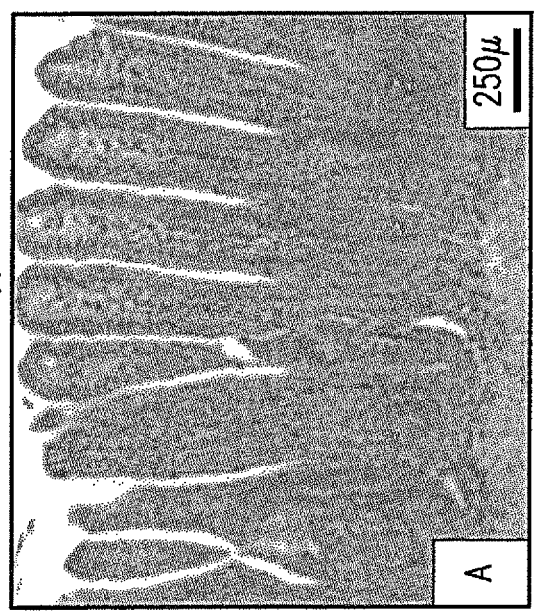

FIG. 3A-C. (A) Photomicrograph of intestinal villi in a wild-type mouse. (B) Photomicrograph of intestinal villi in a Cx43 knockout mouse. (C) migration rate of enterocytes in wild-type versus Cx43 knockout ("ΔIEC").

FIG. 4. Absorption of fat, protein and glucose by WT versus Cx43 knockout mouse intestine.

FIG. 5A-H. (A) Photomicrograph of intestinal tissue of a healthy wild-type mouse; (B) photomicrograph of intestinal tissue of a healthy wild-type mouse stained to show expression of inducible nitric oxide synthase ("iNOS"); (C) photomicrograph of intestinal tissue of a wild-type mouse having NEC; (D) photomicrograph of intestinal tissue of a wild-type mouse having NEC stained to show expression of iNOS; (E) photomicrograph of intestinal tissue of a Cx43 knockout mouse; (F) photomicrograph of intestinal tissue of a Cx43 knockout mouse stained to show expression of iNOS; (G) photomicrograph of intestinal tissue of a Cx43 knockout mouse having NEC; and (H) photomicrograph of intestinal tissue of a Cx43 knockout mouse with NEC stained to show expression of iNOS.

FIG. 6A-B. (A) Migration rate of enterocytes from either wild-type ("WT") healthy (control) mice, wild-type mice having NEC, Cx43 knockout mice ("ΔIEC"), or Cx43 mice having NEC. (B) Cytokine levels of either wild-type or Cx43 knockout mice ("Cx43$^{\Delta IEC}$"), having NEC.

Figure 7A:
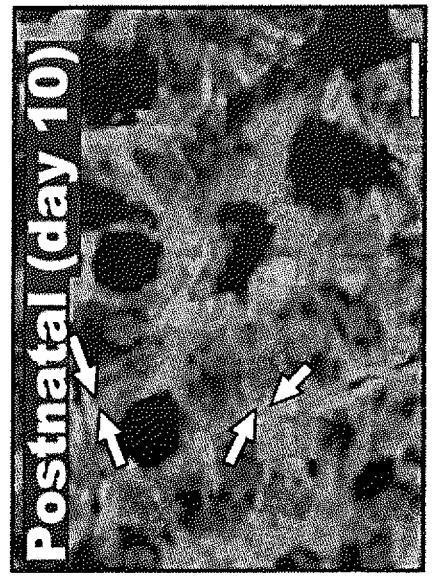
Figure 7B:

FIG. 7A-B. Cx43 expression in (A) premature (gestation day 15.5) or (B) postnatal (day 10) murine intestinal cells, as shown using a fluorescent anti-Cx43 antibody.

FIG. 8A-E. (A) Photomicrograph of control murine intestine. (B) Photomicrograph of murine intestine after exposure to adenoviral vector carrying Green Fluorescent Protein ("GFP") gene. (C) Photomicrograph of murine intestine after exposure to adenoviral vector carrying GFP and dominant negative Cx43 mutant protein ("dnCx43"). (D) Expression of GFP in murine intestine in the presence ("DN") or absence ("WT") of dnCx43. (E) Colitis severity in murine intestine in the presence ("DN") or absence ("WT") of dnCx43.

FIG. 9A-C. Surface mucosa of murine intestine, either (A) control; (B) after exposure to adenoviral vector carrying GFP; or (C) after exposure to adenoviral vector carrying GFP and dnCx43.

FIG. 10A-B. (A) IEC-6 enterocytes were treated with the concentrations of phorbol myristate acetate ("PMA") indicated for one hour and then evaluated for the extent of enterocyte gap junction communication by confocal based dye transfer. The untreated cells represent the 100% dye transfer. *p<0.05 versus untreated cells. (B) IEC-6 cells were treated with the concentration of PMA indicated and assessed for their ability to migrate into a scraped wound over 20 hours. *p<0.05 vs. untreated cells. Representative of two separate experiments.

5. DETAILED DESCRIPTION OF THE INVENTION

For clarity of description, and not by way of limitation, the detailed description of the invention is divided into the following subsections:
(i) gap junction enhancing agents;
(ii) assay methods;
(iii) pharmaceutical compositions; and
(iv) methods of treatment.

5.1 Gap Junction Enhancing Agents

Gap junction enhancing agents ("GJEAs") include gap junction enhancing peptides ("GJPs") and peptide analogs ("GJPAs") as well as other compounds such as pharmacologic agents.

Non-limiting examples of pharmacologic agents that are GJEAs include phorbol myristate acetate ("PMA") and quinoline derivatives as described in United States Patent Publication No. 20090143425, such as, but not limited to, primaquine, mefloquine, PQ2, PQ3, PQ4, PQ5, PQ6, PQ7, PQ8 and/or the compound PQ1:

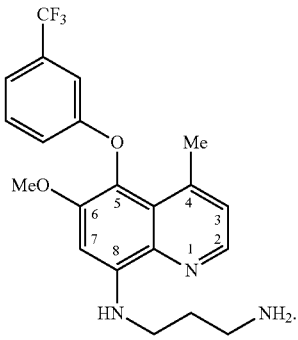 [SMILES: COc1cc(NCCCN)c2nccc(C)c2c1Oc1cccc(C(F)(F)F)c1]

Gap Junction enhancing peptides ("GJPs") that may be used according to the invention include but are not limited to peptides listed in United States Patent Application Publication No. 20090075291 by Delmar et al., which is incorporated by reference in its entirety herein, including: DVPGRDPGYIKGGGSAHARVPFYSHSLNRN-RKPSLYQ (SEQ ID NO:1); EIQPRSPLMFSGGGSAHA-RVPFYSHSAKEARWPRAHR (SEQ ID NO:2); GIAAREPNSHDGGGSAHARVPFYSHSRDLWRK-PAKSL (SEQ ID NO:3); WEEPRRPFTMSGGG-SAETHARVPFYSHSPMRHRLPGVHL (SEQ ID NO:4); SDDLRSPQLHNGGGSAVPFYSHSHMVRRKPRNPR (SEQ ID NO:5); GHLHLRVPTLKM (SEQ ID NO:6); EFIRSPHSVDWL (SEQ ID NO:7); SQSRNPPMPPPR (SEQ ID NO:8); RRPPYRVPPKLF (SEQ ID NO:9); SLY-ERHPASTYP (SEQ ID NO:10); HTVSRRPLPSSG (SEQ ID NO:11); RHTHGNLLRFPP (SEQ ID NO:12); RNNL-NQTYPERR (SEQ ID NO:13); YSLLPVRPVALT (SEQ ID NO:14); RKPTQSLPTRLV (SEQ ID NO:15); TRRPHK-MRSDPL (SEQ ID NO:16); TLTWHTKTPVRP (SEQ ID NO:17); SRQFLHSLDRLP (SEQ ID NO:18); HLHH-HLDHRPHR (SEQ ID NO:19); QTPYQARLPAVA (SEQ ID NO:20); WHPHRHHHLQWD (SEQ ID NO:21); RRK-PRRKP (SEQ ID NO:22); RNPRNP (SEQ ID NO:23); RRKP (SEQ ID NO:24); RRNP (SEQ ID NO:25); RNP or SDDLRSPQLHNHMVRRKPRNPR (SEQ ID NO:26), and also include other peptides and peptide derivatives that enhance gap junction communication between enterocytes.

One non-limiting example of a GJPA is Compound ZP123 (Rotigaptide (2R, 4S)-1-[(2R)-1-[(2R)-2-acetamido-3-(4-hydroxyphenyl)propanoyl]pyrrolidine-2-carbonyl]-N-[2-[[(2R)-1-[(2-amino-2-oxoethyl)amino]-1-oxopropan-2-yl]amino]-2-oxoethyl]-4-hydroxypyrrolidine-2-carboxamide), having the following formula:

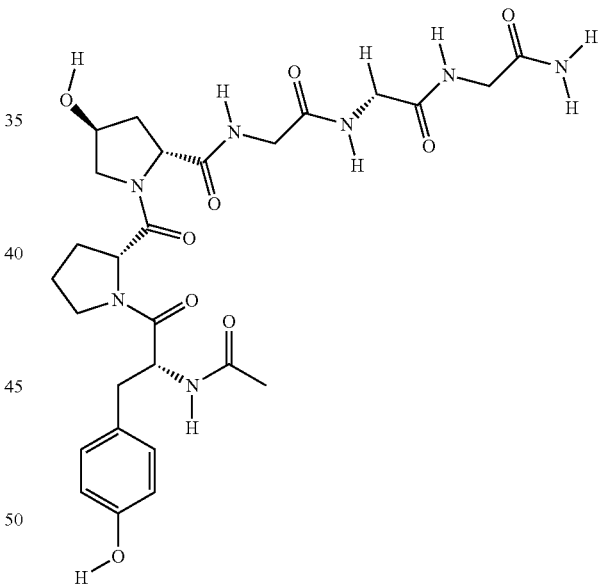

which enhances gap junction connectivity through increased activation of Cx43. The prototypical compound, Rotigaptide, is stable, has a long half-life, and is in clinical trials as an anti-arrhythmic agent in adults, based upon its documented ability to enhance gap junction connectivity.

Further non-limiting examples of GJPs include pharmacophores of Cx43 based upon the "RXP" series of Cx43-binding peptides. These pharmacophores bind to the carboxyl terminal of Cx43, and share a 34-aa peptide (RXP-E (SEQ ID NO:27)) sequence. Two representatives of this family are a cyclized heptapeptide (called CyRP-71) and a linear octapeptide of sequence RRNYRRNY (SEQ ID NO:28).

Another non-limiting example of a GJP that may be used according to the present invention is Gly-Ala-Gly-Hyp-Pro-Tyr-NH$_2$ ("AAP10"; SEQ ID NO:29) and related sequences such as but not limited to Gly-Pro-Hyp-Gly-Ala-Gly (SEQ ID NO:30) or cyclo[CF(3)C(OH)-Gly-Ala-Gly-Hyp-Pro-Tyr (SEQ ID NO:31).

The present invention further provides for peptides that are between 4 and 100, or between 4 and 50, or between 6 and 100, or between 6 and 50, or between 8 and 100, or between 8 and 50, or between 10 and 100, or between 10 and 50, or between 15 and 35, amino acids long and comprise one or more peptide having SEQ ID NO:1-31.

The present invention further provides for peptides that are between 4 and 100, or between 4 and 50, or between 6 and 100, or between 6 and 50, or between 8 and 100, or between 8 and 50, or between 10 and 100, or between 10 and 50, or between 15 and 35, amino acids long and comprise one or more peptide having a sequence which differs from any of SEQ ID NO:1-31 by no more than one amino acid and has a gap junction enhancing activity that is at least 80 percent of a peptide lacking the difference in sequence.

The present invention further provides for peptide analogs ("GJPA") such as compound GAP-134 (i.e. (2S,4R)-1-(2-aminoacetyl)-4-benzamido-pyrrolidine-2-carboxylic acid) or other peptide analogs that enhance gap junction communication between enterocytes. Without being bound by any theory, GAP-134 acts by enhancing gap junction conductance without effects on other ion channels, without any apparent changes in transcription or distribution of Cx43. This compound has a shorter half-life than ZP123, which may decrease its effectiveness, but also may limit potential toxicity;

5.2 Assay Methods

The ability of a GJEA, GJP or GJPA to enhance gap junction communication between enterocytes may be determined by any method known in the art, including in vitro and in vivo studies.

As a non-limiting example, gap junction intercellular communication (GJIC) studies, which assess the ability of a GJEA, GJP or GJPA to enhance gap junction communication between enterocytes, may be performed in vitro in cultured enterocytes, using live cell confocal microscopy and fluorescence recovery after photobleaching (FRAP), as in (1, 2). For example, cells may be plated to confluence, and treated with a GJEA, GJP or GJPA for times between 1-4 hours, and the degree of gap junction intercellular communication may be determined using confocal based fluorescence recovery after photobleaching (FRAP), which measures the movement of a fluorescent tracer through gap junctions into an area that has been previously photobleached using a laser, such that the rate and extent to which the photobleached cells fill with the fluorescent dye (termed the "fluorescence recovery") may provide a direct measure of gap junction activity.

A second non-limiting example of a method for assessing the ability of a GJEA, GJP or GJPA to enhance gap junction communication between enterocytes is single cell microinjection (2), which allows the detection of the extent to which a detectable tracer, for example the 0.4 kilodalton fluorescent gap junction tracer Lucifer yellow, passes from an injected cell to adjacent cells through gap junctions.

As one specific non-limiting example, IEC-6 cells may be used for such studies, as they represent a well validated culture model of the intestine. Non-limiting examples of other cell lines that may be used include HT-29 and CaCO-2 cells.

In certain non-limiting embodiments of the invention, the ability of a GJEA, GJP or GJPA to treat NEC may be assessed in vivo by the following study in mice.

a. Power analysis: Sample size estimates may be conducted using the nQuery Advisor 3.0 software (Statistical Solutions, Saugus, Mass.), with $\alpha=0.05$, and differences in proportions between Groups averaging 0.22 with a variance of 0.029 and an effect size of 0.167 yielding 15 animals per group to attain 80% power. An estimated 20% of the animals would not be expected to survive, therefore the sample size should be increased to 18 to account for mortality loss. Experiments performed in triplicate with 18 mice per group, 4 groups per experiment=216 mice.

b. Induction of experimental NEC: NEC may be induced in 10-day old wild-type mice. Mice may be administered 15 g Similac 60/40 (Ross Pediatrics) in 75 mL of Esbilac canine milk replacer (Pet-Ag Inc) as well as hypoxia (5% oxygen for 2 minute prior to each feeding) twice daily for four days. Animals may be fed 200 microliters per 5 grams of mouse body weight by gavage over 2-3 minutes, using a 24-French angiocatheter which is placed into the mouse esophagus under direct vision. Samples of the terminal ileum 2 cm away from the ileocecal valve may then be harvested at day four for analysis. Control (i.e. non NEC) animals may remain with their mothers and receive breast milk.

c. Timing of administration of gap junction peptides: animals may be treated with GJEA, GJP or GJPA prior to the induction of experimental NEC; for example at varying doses, twice daily for either 1, 2, 3 or 4 days prior to the induction of NEC. Morbidity in animals that receive GJEA, GJP or GJPA alone should be assessed. Peptides may be administered via the i.p (intraperitoneal) or the p.o. (oral) route d. Assessment of the severity of experimental NEC: The extent of NEC that develops may be assessed by measuring 1) histopathological evidence of mucosal damage. 2) serum IL-6 as determined by ELISA. 3) RT-PCR to assess the expression of IL-6, IL-8 and TNF-$\alpha$ in the mucosal scrapings, for example using mouse specific primers.

In certain non-limiting embodiments of the invention, the ability of a GJEA, GJP or GJPA to treat IBD may be assessed in vivo by the following study in mice.

a. Power analysis: Sample size estimates may be conducted using the nQuery Advisor 3.0 software (Statistical Solutions, Saugus, Mass.), with $\alpha=0.05$, and differences in proportions between Groups averaging 0.22 with a variance of 0.029 and an effect size of 0.167 yielding 15 animals per group to attain 80% power. There is essentially no mortality in the colitis model, and the sample size may be 25 per group. Total mice: experiments in triplicate, 4 groups, 25 per group—300 mice.

b. Induction of experimental colitis: Colitis may be induced in 4 week old mice using the dextran sodium sulfate model. 4% DSS may be administered in the drinking water for 5 days, at which point 100% of mice develop inflammation of the mucosa of the colon, associated with infiltration of inflammatory cells.

c. Timing of administration of gap junction peptides: animals may be treated with GJEA, GJP or GJPA prior to the induction of colitis; animals may be administered GJEA, GJP or GJPA for varying doses, twice daily for either 1, 2, 3 or 4 days prior to the induction of colitis. Morbidity in animals that receive GJEA, GJP or GJPA alone should be assessed. GJEA, GJP or GJPA may be administered via the i.p or the p.o. route d. Assessment of the severity of experimental colitis: The extent of colitis that develops may be assessed by measuring 1) histopathological evidence of mucosal damage. 2) serum IL-6 as determined by ELISA. 3) RT-PCR to assess the expression of IL-6, IL-8 and TNF-α in the mucosal scrapings, for example using mouse specific primers.

The foregoing methods may be used to determine whether a particular concentration of a GJEA, GJP or GJPA is able to enhance gap junction communication between enterocytes, to reduce the incidence of NEC, to treat NEC, to reduce the incidence of IBD, or to treat IBD.

In non-limiting embodiments of the invention, aGJEA, GJP or GJPA enhances (increases the rate or amount of) communication between adjacent enterocytes by at least about 10 percent, or at least about 20 percent, or at least about 30 percent, or at least about 40 percent, or at least about 50 percent, or at least about 60 percent, or at least about 70 percent, or at least about 80 percent, or at least about 100 percent, relative to the amount of communication under control conditions (e.g. the absence of the GJEA, GJP or GJPA).

5.3 Pharmaceutical Compositions

The present invention provides for a pharmaceutical composition comprising one or more GJEA, GJP or GJPA in a pharmaceutically suitable carrier.

Said pharmaceutical composition may be in solid or liquid form.

In non-limiting embodiments of the invention, a pharmaceutical composition may comprise GJEA, GJP or GJPA which is optionally lyophilized or comprised in micelles or microspheres.

In non-limiting embodiments of the invention, a pharmaceutical composition may comprise GJEA, GJP or GJPA in a solvent such as but not limited to water, saline, and/or a physiologic buffer, for example, but not limited to, a phosphate buffer, an acetate buffer, a carbonate buffer, a glutamate buffer, a glycinate buffer, a histidine buffer, a lactate buffer, a succinate buffer, a maleate buffer, a tartrate buffer, a Tris buffer, or a citrate buffer.

Non-limiting examples of other ingredients which may optionally be included in pharmaceutical compositions of the invention include albumin, ascorbic acid, sodium bisulphite, sodium metabisulphite, sodium sulphite, thioglycerolm thioglycolic acid, cysteine, ethylene diametetraacetic acid, citric acid/sodium citrate, ethylene glycol, glycerol, glucose, dextran, and/or a surfactant, for example sodium dodecyl sulfate, Polysorbate 80, and/or Polysorbate 20.

In a set of specific non-limiting embodiments of the invention, one or more GJEA, GJP or GJAP may be comprised in an infant nutritional formula, considered a pharmaceutical formulation and also a so-called "nutriceutical" formulation, which may be administered to an infant suffering from NEC or at risk of developing NEC to treat or reduced the risk of NEC in the infant. Such infant nutritional formula may, for example and not by way of limitation, further comprise one or more of casein, whey protein, soy lecithin, lactose, dextrose, sodium chloride, potassium chloride, calcium carbonate, ferrous sulfate, ascorbic acid, vitamin A, vitamin B6, vitamin B12, vitamin D3, thiamine, vitamin E, and/or vitamin K.

5.4 Methods of Treatment

In non-limiting embodiments, the present invention provides for a method of treating NEC in a subject in need of such treatment comprising administering to the subject an effective amount of a GJEA, GJP or GJPA.

In other non-limiting embodiments, the present invention provides for a method of treating IBD in a subject in need of such treatment comprising administering to the subject an effective amount of a GJEA, GJP or GJPA.

In other non-limiting embodiments, the present invention provides for a method of reducing the risk of occurrence of NEC in a subject in need of such treatment comprising administering to the subject an effective amount of a GJEA, GJP or GJPA.

In other non-limiting embodiments, the present invention provides for a method of reducing the risk of occurrence of IBD in a subject in need of such treatment comprising administering to the subject an effective amount of a GJEA, GJP or GJPA.

A subject may be a human or non-human subject, including but not limited to a dog, cat, rodent, cow, sheep, goat, horse, or non-human primate. In non-limiting embodiments the subject is a human infant. In non-limiting embodiments the subject is a human infant born after less than 40 weeks or less than 37 weeks or less than 30 weeks or less than 25 weeks gestation.

IBD as that term is used herein refers to disorders including but not limited to Crohn's disease, ulcerative colitis, lymphocytic colitis, ischemic colitis, Behçet's disease, diversion colitis, and irritable bowel syndrome.

A GJEA, GJP and/or GJPA, for example as comprised in a pharmaceutical formulation, may be administered by any route known in the art, including but not limited to oral, intravenous, intraperitoneal, inhalation (nasal and pulmonary), subcutaneous, intramuscular, or rectal. It may be desirable to promote local rather than systemic delivery of a GJEA, GJP or GJPA so as to limit the effect of the agent on gap junctions outside the intestine, for example by selecting a method of administration such as oral or rectal and/or by providing a sustained release formulation.

Non-limiting examples of dosages include an amount that results in a local concentration at the intestinal mucosa between 10 and 200 nMol/L, or between 0.125 and 1 mM, or a dosage from 0.05 to 10 mg/kg or between 0.05 and 5 mg/kg or between 0.1 and 1 mg/kg. Dosages may, in non-limiting embodiments, be administered once, twice, three or four times daily, or every other day, or once a week, or once every two weeks, or once a month.

"Treating" means reducing the objective and/or subjective symptoms or signs of the disease being treated, including but not limited to one or more of: a decrease in intestinal tissue viability, malabsorption, diarrhea, bleeding, loss of electrolytes, return to normal activities of daily living and pain. In non-limiting embodiments the reduction is of a magnitude of at least about 20 percent or at least about 30 percent or at least about 40 percent or at least about 50 percent.

In non-limiting embodiments, "reducing the risk" of occurrence means a reduction in risk of at least about 10 percent or at least about 20 percent or at least about 30 percent or at least about 40 percent or at least about 50 percent.

6. EXAMPLE 1: SUSCEPTIBILITY TO NEC OF CX43 KNOCKOUT MICE

Enterocyte-specific Cx43 knockout mice were generated using the Cre/loxP system, where Cx43 loxp/loxp mice were generated and crossed with villin-cre mice. The effectiveness of the "knockout" was documented by RT-PCR (FIG. 1). As further confirmation, intestinal tissue of these mice was stained with detectable antibodies directed toward either Cx43 or actin, and the relative absence of Cx43 was apparent (FIG. 2B).

Enterocytes from the knockout mice were observed to be morphologically and functionally impaired relative to normal enterocytes. As shown in FIGS. 3B and 3A, respectively, the intestinal villi in the Cx43 knockout animals were substantially shortened compared with control intestine. Moreover, enterocytes from the knockout animals ("ΔIEC") demonstrated lower migration rates (FIG. 3C). As shown in FIG. 4, Cx43 knockout mice were less able to absorb fat from their diet.

Enterocyte-specific Cx43 knockout mice were observed to manifest increased susceptibility to NEC. NEC was induced in wild-type control mice and Cx43 knockout animals using a protocol that combines gavage feeding and hypoxia for 4 days. When exposed to the same conditions, the intestinal tissue of Cx43 knockout mice showed substantially more dramatic alteration relative to wild type (compare FIGS. 5G and 5C), with substantially greater induction of inducible nitric oxide synthase (iNOS), a marker of inflammation (compare FIG. 5H with FIG. 5D). The enterocytes in the NEC-induced Cx43 knockout animals exhibited a slower migration rate (FIG. 6A) and inflammatory cytokine levels IL-6, TNF, and IL-1 were all substantially higher (FIG. 6B).

The above findings support an association between NEC and Cx43 deficiency and gap junction dysfunction.

7. EXAMPLE 2: CX43 IN PREMATURE BOWEL

It was observed that Cx43 expression is reduced in the eneterocytes of mouse embryos on day e15.5 (FIG. 7A) relative to eneterocytes of mice at postnatal day 10 (FIG. 7B). As the incidence of NEC is increased in premature, versus full term, human infants, the observation of lower levels of Cx43 in the "premature" intestine is consistent with a model in which Cx43 deficiency and consequent gap junction dysfunction increases susceptibility to NEC.

8. EXAMPLE 3: HIGHER LEVELS OF CX43 CORRELATE WITH LESS COLITIS

Experiments were performed using adenovirus to introduce dominant negative mutant Cx43 ("dnCx43") into murine enterocytes and thereby create a functional Cx43 deficiency. Adenoviruses carrying dnCx43 with detectable marker GFP were constructed, as were adenoviruses carrying only GFP to serve as controls. Virus was introduced into wild-type mice by rectal administration to produce GFP and GFP/dnCx43 animals. Photomicrographs in FIGS. 8B and 8C show enterocytes of mice infected with adenovirus carrying GFP only or GFP and dnCx43, respectively, where the presence of fluorescence in these figures relative to FIG. 8A demonstrates successful viral infection.

Figure 8D:
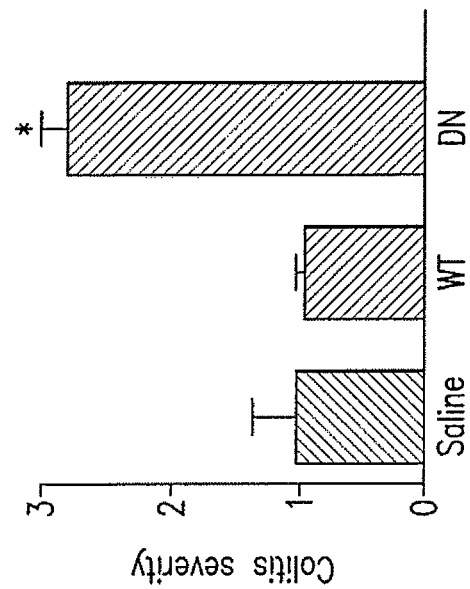
Figure 8E:
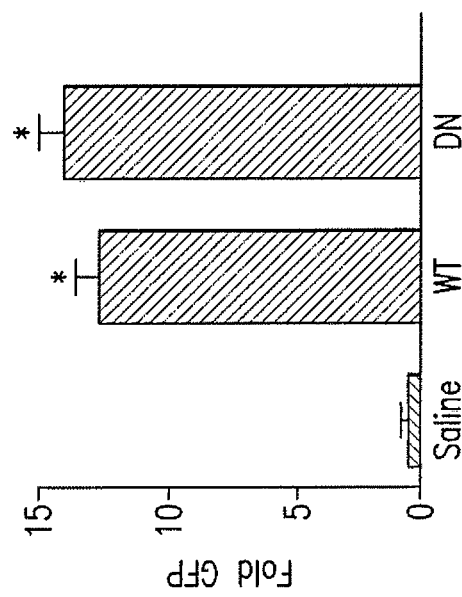

Next, colitis was induced in GFP, GFP/dnCx43 and control animals by administration of dextran sulphate sodium. Cx43 deficiency and consequent gap junction dysfunction and susceptibility to NEC. Visualization of the intestinal mucosa in these animals is shown in FIG. 9A-C. The most severe colitis was observed GFP/dn-Cx43 mice (FIGS. 8E and 9C).

According to these studies, the relatively greater amount of Cx43 in animals that had not received dnCx43 was protective against colitis.

9. EXAMPLE 4: GAP JUNCTION ENHANCER PMA PROMOTES ENTEROCYTE MIGRATION

IEC-6 enterocytes were treated with various concentrations of phorbol myristate acetate ("PMA") for one hour and then evaluated for the extent of enterocyte gap junction communication by confocal based dye transfer. As shown in FIG. 10A, as concentrations of PMA increased, so did the extent of gap junction communication. Further, IEC-6 cells were treated with the concentration of PMA indicated and assessed for their ability to migrate into a scraped wound over 20 hours. As the concentration of PMA increased, the speed (rate) of enterocyte migration also increased, consistent with an association between gap junction enhancement and migration (and consequent healing) within the intestinal mucosa (FIG. 10B).

7. REFERENCES

1. Leaphart et al., 2008, Interferon-gamma inhibits enterocyte migration by reversibly displacing connexin43 from lipid rafts. Am J Physiol Gastrointest Liver Physiol 295: G559-569.
2. Leaphart et al., 2007, Interferon-[gamma] inhibits intestinal restitution by preventing gap junction communication between enterocytes. Gastroenterology 132: 2395-2411.
3. Goodenough, 1974, Bulk isolation of mouse hepatocyte gap junctions. Characterization of the principal protein, connexin, J. Cell Biol. 61:557-563.
4. Goodenough, 1975, The structure of cell membranes involved in intervellular communication. Am. J. Clin. Pathol. 63:636-645.
5. Laird, 2005, Connexin phosphorylation as a regulatory event linked to gap junction internalization and degradation. Biochim. Biophys. Acta 1711:172-182.
6. Lampe et al., 2000, Phosphorylation of connexin-43 on serine 368 by protein kinase C regulates gap junction communication. J. Cell Biol. 149:1503-1512.
7. Verma et al., 2009, Novel pharmacophores of connexin43 based on the "RXP" series of Cx43-binding peptides, Circ Res. 105(2):176-84.

Various publications are cited herein, the contents of which are hereby incorporated by reference in their entireties.

What is claimed is:

1. A method of treating necrotizing enterocolitis in a subject in need of such treatment comprising administering to the subject one or more dose of a gap junction enhancing agent, wherein the one or more dose of the gap junction enhancing agent is between 0.05 mg/kg and 10 mg/kg, and wherein the gap junction enhancing agent is selected from the group consisting of
   (a) a peptide comprising a sequence selected from the group consisting of SEQ ID NO:1-31; and
   (b) a peptide analog selected from the group consisting of rotigaptide and GAP-134 ((2S,4R)-1-(2-aminoacetyl)-4-benzamido-pyrrolidine-2-carboxylic acid).

2. The method of claim 1 where the gap junction enhancing agent comprises a peptide having a sequence selected from the group consisting of SEQ ID NO:1-31.

3. The method of claim 1 where the gap junction enhancing agent is rotigaptide.

4. A method of reducing the risk of occurrence of necrotizing enterocolitis in a subject in need of such treatment comprising administering to the subject one or more dose of a gap junction enhancing agent, wherein the one or more dose of the gap junction enhancing agent is between 0.05 mg/kg and 10 mg/kg, and wherein the gap junction enhancing agent is selected from the group consisting of
   (a) a peptide comprising a sequence selected from the group consisting of SEQ ID NO:1-31; and
   (b) a peptide analog selected from the group consisting of rotigaptide and GAP-134 ((2S,4R)-1-(2-aminoacetyl)-4-benzamido-pyrrolidine-2-carboxylic acid).

5. The method of claim 4 where the gap junction enhancing agent comprises a peptide having a sequence selected from the group consisting of SEQ ID NO:1-31.

6. The method of claim 4 where the gap junction enhancing agent is rotigaptide.

7. A method of inducing increased migration of enterocytes in a subject diagnosed with necrotizing enterocolitis, the method comprising administering to the subject one or more dose of a gap junction enhancing agent, wherein the one or more dose of the gap junction enhancing agent is between 0.05 mg/kg and 10 mg/kg, and wherein the gap junction enhancing agent is selected from the group consisting of
   (a) a peptide comprising a sequence selected from the group consisting of SEQ ID NO:1-31; and
   (b) a peptide analog selected from the group consisting of rotigaptide and GAP-134 ((2S,4R)-1-(2-aminoacetyl)-4-benzamido-pyrrolidine-2-carboxylic acid).

8. The method of claim 7 where the gap junction enhancing agent comprises a peptide having a sequence selected from the group consisting of SEQ ID NO:1-31.

9. The method of claim 7 where the gap junction enhancing agent is rotigaptide.

10. The method of claim 1, wherein the one or more dose of the gap junction enhancing agent is between 0.05 mg/kg and 5 mg/kg.

11. The method of claim 10, wherein the one or more dose of the gap junction enhancing agent is between 0.1 mg/kg and 1 mg/kg.

12. The method of claim 4, wherein the one or more dose of the gap junction enhancing agent is between 0.05 mg/kg and 5 mg/kg.

13. The method of claim 12, wherein the one or more dose of the gap junction enhancing agent is between 0.1 mg/kg and 1 mg/kg.

14. The method of claim 7, wherein the one or more dose of the gap junction enhancing agent is between 0.05 mg/kg and 5 mg/kg.

15. The method of claim 14, wherein the one or more dose of the gap junction enhancing agent is between 0.1 mg/kg and 1 mg/kg.

* * * * *